United States Patent [19]

Trost et al.

[11] 4,307,241

[45] Dec. 22, 1981

[54] RING EXPANSION AND CHAIN EXTENSION PROCESS AND REAGENTS

[75] Inventors: Barry M. Trost; John E. Vincent, both of Madison, Wis.

[73] Assignee: Wisconsin Alumni Research Foundation, Madison, Wis.

[21] Appl. No.: 165,768

[22] Filed: Jul. 3, 1980

[51] Int. Cl.$^3$ .............................................. C07F 7/08
[52] U.S. Cl. ................................. 556/428; 556/488; 568/375
[58] Field of Search ............................. 556/428, 488

[56] References Cited

U.S. PATENT DOCUMENTS 2,715,113  8/1955  Gordon ........................... 556/488 X
3,141,898  7/1964  Tiers ................................ 556/428
3,231,594  1/1966  Speier ............................ 556/488 X

FOREIGN PATENT DOCUMENTS 541829  6/1957  Canada ............................. 556/488

Primary Examiner—Paul F. Shaver
Attorney, Agent, or Firm—McDougall, Hersh & Scott

[57] ABSTRACT

Expansion of a ring structure and extension of a noncyclic structure containing a ketosulfone grouping in the ring by reaction with a 2-X-alkyl-3-allyl-trialkylsilane intermediate in which X is a leaving group and conversion to an expanded ring.

11 Claims, No Drawings

RING EXPANSION AND CHAIN EXTENSION PROCESS AND REAGENTS

The Government has rights in this invention pursuant to Grant Nos. NSF CHE 76-15113, 79-50005 and IPA No. 0001 awarded by the National Science Foundation, and Grant Nos. NIH GM 13598 and GM 7435-01 awarded by the Department of Health, Education, and Welfare.

This invention relates to a process for ring expansion and chain extension of organic compounds and it relates more particularly to reagents used in a new and novel ring expansion and chain extension process and to new and novel compounds produced thereby.

The invention involves the reaction of a ring compound having a keto sulfone grouping

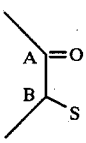

with a reagent having the structural formula

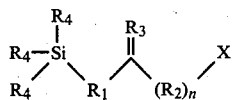

in which S is an aromatic or alkyl sulfonyl group as represented by $SO_2Ph$ or $SO_2CH_3$, $R_1$, $R_2$, and $R_3$ are carbon groups, with or without alkyl substitution, $R_4$ is a $C_1-C_{18}$ aliphatic or cyclic group, such as methyl, ethyl, propyl, in which one and preferably all of the $R_4$ groups are such alkyl groups, n is a number between 1 and 3 and most frequently 1 and X is a leaving group. The leaving groups are well known to the skilled in the art, reference being made to standard textbooks such as the test entitled "Introduction to Organic Chemistry" by Streitwieser and Heathcock, published by McMillan Publishing Company, and exemplified by such leaving groups represented by halogen (e.g. chlorine and bromine), sulfonate esters and the like.

The A and B positions in the ring are the two active positions on which the reaction takes place to add the reagent as represented by the following reaction

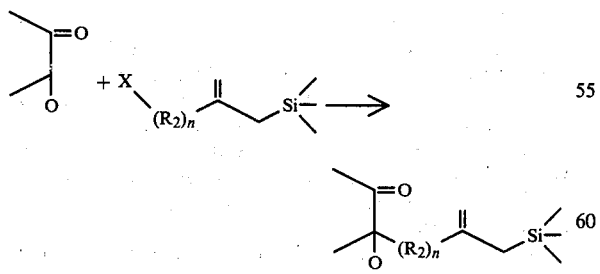

when n is 1, three carbons are added to the ring, when n is 2, four carbons are added, and when n is 3, five carbons are added.

The extended compound can be reformed into a ring in the form of a methylenecycloalkane upon removal of the silicon group in the presence of fluoride ion as depicted by the following equation

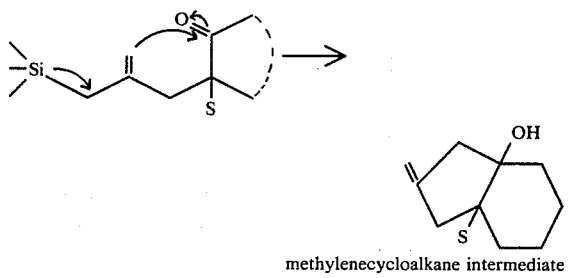

methylenecycloalkane intermediate

The common bond in the intermediate product that is formed can cleave or be induced to cleave by base to a stable ring structure having 3, 4 or 5 additional members depending on whether n is 1, 2 or 3 respectively. This cleavage fails if the initial β-ketosulfone is part of a simple six or seven membered ring. In the case of the starting compound being a five membered ring, cleavage of the bond requires the addition of an alkyl metal hydride such as potassium hydride such as represented by the following equation:

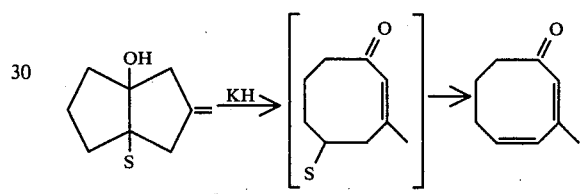

The initial alkylation reaction is carried out in a solution in the presence of a base such as an alkali metal hydride (and alkali metal iodide as catalyst when a sulfonate ester is used as a leaving group) for a time ranging from 1 to 36 hours and at a temperature within the range of room temperature to about 75° C. and preferably at a temperature within the range of 50°-70° C.

The reagent from which the additions are made to the ring structure is believed to be a new and novel compound which may be identified further as 2X-alkyl-3-allyl trialkyl silane as represented by 2-iodo-methyl-3-allyl trimethyl silane,
2-iodo-methyl-3-allyl triethyl silane,
2-chloro-methyl-3-allyl trimethyl silane,
2-chloro-ethyl-3-allyl trimethyl silane,
2-methanesulfonato-methyl-3-allyl trimethyl silane,
2-iodo-propyl-3-allyl-trimethyl silane.

Formation of the intermediate is carried out in the presence of a halide ion such as a fluoride ion while in solution in a suitable solvent such as tetrahydrofuran.

Bond cleavage in the cyclic intermediate and formation of the expanded ring occurs only when the release of strain energy in the original intermediate is exothermic when going to the enlarged ring product. If the release of strain energy is not exothermic, the ring expansion will not result.

In the illustrated modification wherein the starting β-keto sulfone is other than a five, six, or seven membered ring, the first formed cyclic intermediate immediately fragments and the SO₂Ph carbon picks up the proton as illustrated in the following equation

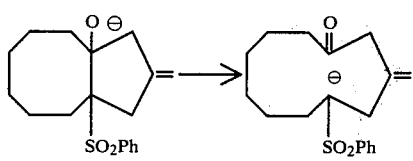

Proton migration forms an enolate (which may be silylated) and subsequently the conjugated enone after workup as follows

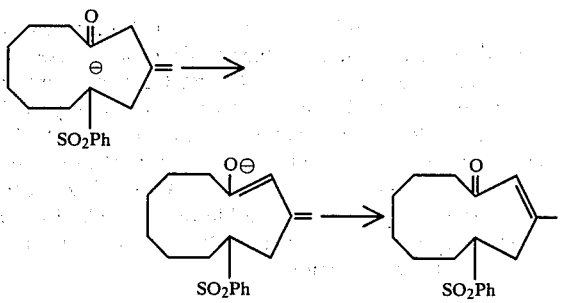

Having described the basic mechanics of the reactions of the invention, illustration will be made by reference to the following examples, which are given by way of illustration and not by way of limitation.

EXAMPLE 1

The following is an example of the general alkylation procedure for chain extension in accordance with the practice of this invention.

The keto-sulfone is represented by the general formula

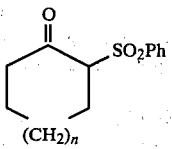

in which n equals 3.

To a suspension of 28.8 mg sodium hydride (1.2 mmol) and 180 mg sodium iodide (1.20 mmol) in 0.7 ml anhydrous dimethylformamide (DMF), under nitrogen, addition is made of 1.26 mmol of the keto-sulfone in a minimal quantity of anhydrous DMF. The mixture was heated to 55° C. for 30 minutes to ensure complete solution of the sulfone. The solution was cooled to room temperature and a solution of the mesylate reagent in the form of 2-methanesulfonato-3-allyl trimethyl silane in the amount of 266 mg. (1.2 mmol) in 1.0 ml anhydrous DMF was added. The reaction mixture was heated to 55° C. and maintained at that temperature for from 2 to 12 hours.

Upon completion of the reaction, the mixture was rinsed into a separatory funnel with 20 ml ethyl ether plus 2 ml water and the ethereal phase was separated. The aqueous phase was extracted with another 20 ml ethyl ether and the ethereal extracts were then combined, washed with 10 ml of brine and dried over MgSO₄, filtered and then concentrated under vacuum to yield a product having the general formula

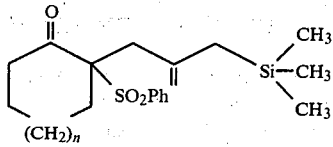

Chromatography on PTLC plates (Hex: ethyl ether systems) indicates approximately a 75–80% yield of the C-alkylated product and only a trace of the O-alkylated analog.

EXAMPLE 2

When n equals 4, the suspension of sodium hydride (36 mg, 1.5 mmol) and sodium iodide (45 mg, 0.30 mmol) in 1 ml anhydrous 1,2-dimethoxyethane (DME) was added under nitrogen to a solution of the keto-sulfone in the amount of 1.575 mmol in a minimal volume of anhydrous DME. The reaction mixture was heated to 60°–65° C. for 15 minutes to insure solution of the enolate. The mesylate reagent was added in an amount of 333 mg (1.5 mmol) in 1 ml anhydrous DME. The reaction mixture was heated to 60°–65° C. and maintained at that temperature for 36 hours. The workup and analysis, as in the preceding example, indicates a yield of 74–80% of the desired C-alkylated product with only a trace of O-alkylation.

The mesylate reagent is believed to represent a new and novel compound. The preparation of the mesylate will be represented by the following example in which the $R_4$ group of the structural formula is illustrated by methyl groups and the leaving X group is represented by the sulfonate ester

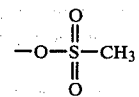

EXAMPLE 3

To a solution of the alcohol (CH₃)₃Si⌒⌒OH (1.44 g, 10.0 mmol) and triethylamine (1.12 g, 11.0 mmol) in 120 ml anhydrous methylene dichloride (CH₂Cl₂) at 0° C., addition was made of 1.26 g (11 mmol) of methanesulfonyl chloride (CH₃SO₂Cl). The reaction mixture was maintained at 0° C. for 30 minutes after which no alcohol remained. The cooled solution was washed with brine (60 ml), dried with MgSO₄, filtered and concentrated under vacuum to yield the mesylate which was then chromatographed on 150 g Grace SG (60–200 ml) using methylene dichloride as eluent. This yielded a clear oil as a pure product in the amount of 1.65 g (74.3% yield).

ir (CHCl₃): 3010, 2975, 2895, 1640, 1460, 1420, 1370, 1320, 1270, 1195, 1170, 1030, 995, 960, 875, 795, 770, 740, 715, 675.

nmr (C11Cl₃): δ0.03 (s, 9H), 1.55 (s, 2H), 2.98 (s, 3H), 4.55 (s, 2H), 4.82 (s, 1H), 5.01 (s, 1H).

In the foregoing example the methyl groups on the silicon atom can be replaced with one or more other C₁-C₁₈ aliphatic or alicyclic groups, and the sulfonate ester can be replaced with other sulfonate ester groups in which the methyl group is replaced with an aliphatic or cyclic group as defined above.

The corresponding derivative, to replace the sulfonate ester with a leaving group, as represented by an iodide ion, is prepared by substitution of an iodide ion for the sulfonate ester. The reactions of example 3 are represented by the following equations to yield 2-iodomethyl-3-allyl trimethylsilane.

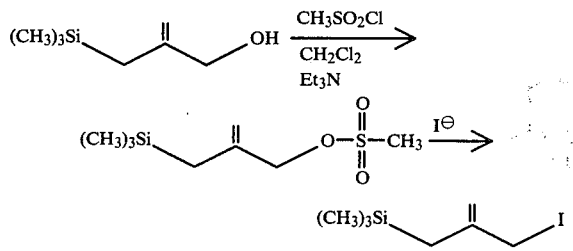

EXAMPLE 4

This example will illustrate the preparation of muscone by chain extension and ring expansion in accordance with the practice of this invention.

EXAMPLE 4a

To a suspension of sodium hydride (14.4 mg, 0.6 mmol) and sodium iodide (18 mg, 0.12 mmol) in 0.36 ml anhydrous DME, addition was made of a solution of a keto-sulfone (2-benzene-sulfonylcyclododecanone) (1) (203 mg, 0.63 mmol) in 1.6 ml anhydrous DME. The mixture was heated to 55° C. to effect complete dissolution. The mesylate 2-methanesulfonato-3-allyl trimethyl silane in an amount of 133.2 mg, (0.60 mmol) in solution in 0.3 ml anhydrous DME was added to the solution and heated to 65° C. for 6 hours. The temperature was reduced to 55° C. and maintained at that temperature for an additional 12 hours. After a total of 36 hours, the reaction was quenched with 1 ml H$_2$O, rinsed into a separatory funnel with 15 ml ethyl ether and the organic phase was separated. The aqueous phase was extracted with another 15 ml ethyl ether. The ethereal extracts were combined, dried with MgSO$_4$ and concentrated under vacuum to a crude oil, which, after chromatography on a 20×20 PTLC plate, (Hex: Et$_2$O=10:2) gave the desired C-alkylated product in a yield of 233 mg and identified as 2-benzenesulfonyl 2-(2'-trimethylsilylmethyl-3'-allyl) cyclododecanone. (2)

ir (CHCl$_3$): 3060, 2920, 2860, 1708, 1628, 1470, 1450, 1308, 1250, 1100, 1080, 855, 790, 760, 720, 690.

nmr (CCl$_4$): δ 0.03 (s9H), 1.20–2.20 (m, 20H), 2.40 (s, 2H), 2.40–2.80 (m, 2H), 4.53 (s, 1H), 4.59 (s, 1H), 7.55 (m, 3H), 7.72 (d, 2H, J=8Hz).

EXAMPLE 4b

To a solution of the C-alkylated product of example 4a, in the amount of 586 mg (1.308 mmol) in 7.7 ml anhydrous tetrahydrofuran (THF), addition was made of tetra-n-butylammonium fluoride in the amount of 68.3 mg (0.262 mmol) and the solution was heated to 55° C. for 1 hour. The reaction mixture was then rinsed into a separatory funnel with 50 ml ethyl ether and 10 ml water. The ethereal layer was separated and the residual aqueous layer was extracted with another 50 ml ethyl ether. The ethereal extracts were combined, dried with MgSO$_4$, filtered and then concentrated under vacuum to give a crude oil. Chromatography on a 20×40 cm PTLC plate (Hex: Et$_2$O=10:6) yielded the enone-sulfone as a mixture of geometric isomers, mp 90°–92° C. and 104°–107° C. Of the starting 12 membered ketone, 19.3% was recovered giving a overall yield of the desired macrocycle of 75.6% at 80.7% conversion represented by the formula

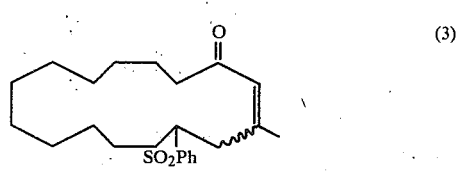

ir (CHCl$_3$): 3058, 2930, 2858, 1686, 1618, 1450, 1450, 1395, 1370, 1306, 1228, 1100, 1088, 1030, 1000, 920, 780, 760, 730, 695, 620.

nmr (CDCl$_3$): δ 1.22 (bs, 14H), 1.50–3.20 (m, 9H), 2.07 (s, 3H), 6.16 (bs, 1H), 7.40–7.65 (m, 3H), 7.80–7.96 (m, 2H).

By way of further examples, any of the 2-X-alkyl-3-allyltrialkyl silanes heretofore described may be substituted in equal amounts, in whole or in part, for the 2-methanesulfonato-3-allyl trimethyl silane of example 4a.

EXAMPLE 4c 190 mg (0.505 mmol) of the enone (4) was dissolved in 15 ml absolute ethyl alcohol containing 190 mg 5% Pd on BaSO$_4$ catalyst. The solution was hydrogenated at atmospheric pressure for 1 hour, after which the catalyst was removed by filtration. The residual solution was concentrated in vacuum to give 190 mg of keto sulfone (4)

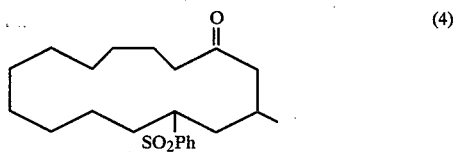

ir (C$_4$Cl$_3$): 2925, 2855, 1710, 1460, 1445, 1370, 1300, 1148, 1085, 1060, 730, 690.

nmr (CDCl$_3$): δ 0.80 & 0.90 (2 doublets, diast.—CH$_3$'s, total 3H, J=6Hz in each), 1.20–1.65 (m, 21H), 2–2.4 (m, 4H), 2.90 (b mult, 1H), 7.45 (m, 3H), 7.78 (m, 2H).

EXAMPLE 4d 190 mg (0.503 mmol) of the sulfone of example 4b was dissolved in 20 ml absolute methanol and addition was made of 2.57 g anhydrous disodium hydrogen phosphate (Na$_2$HPO$_4$) and 10.26 g of 6% sodium amalgam Na(Hg). The mixture was stored overnight at room temperature. The mixture was filtered, the filtrate was concentrated under vacuum, and the residue was taken up with 50 ml diethyl ether (Et$_2$O) and 15 ml. water. The ethereal extract was separated and the aqueous phase was again extracted with another 25 ml of diethyl ether. The ethereal phases were combined, dried with MgSO$_4$ and filtered. The filtrate was concentrated under vacuum to yield 113 mg of a pure oily product, 3-methylcyclopentadecanone (muscone) (5), identical to an authentic sample.

The following equations illustrate the reactions in the preparation of Muscone in accordance with the examples 4a–4d.

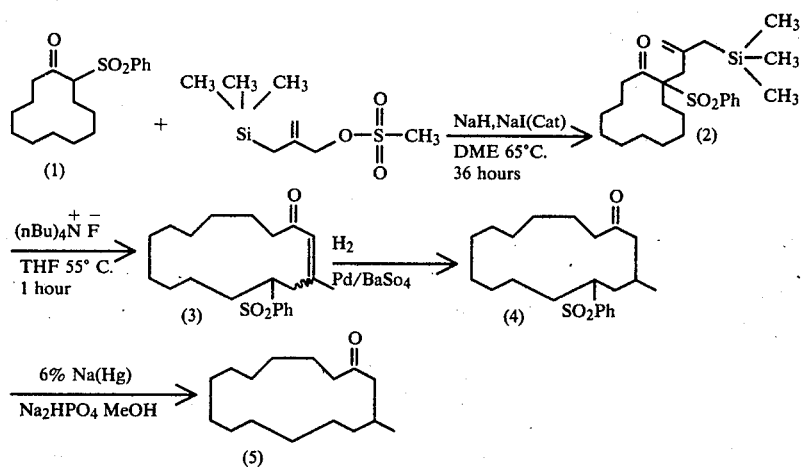

Other examples are illustrated by the following equations and identified in the corresponding tables which show the reactants and reaction conditions for carrying the original ketosulfone to the corresponding chain extention product, in accordance with the practice of this invention, followed by cyclization of the extended chain to the corresponding ring extended product.

In the following equations,

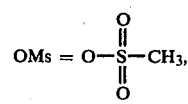

and TMS=$(CH_3)_3Si$.

Example 5

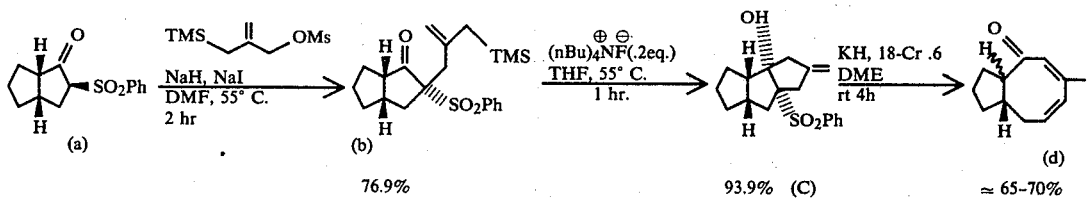

Example 6

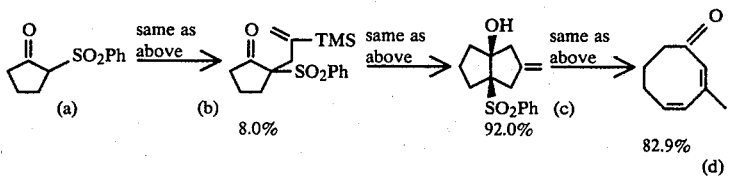

Example 7

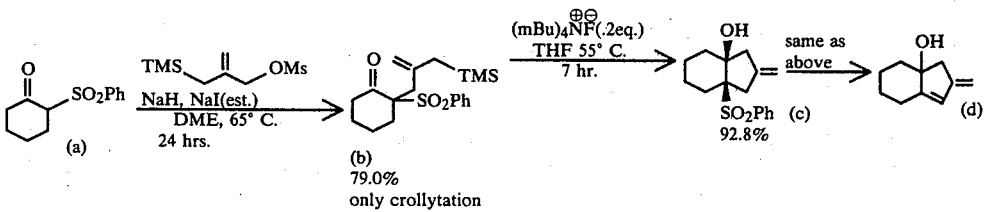

Example 8

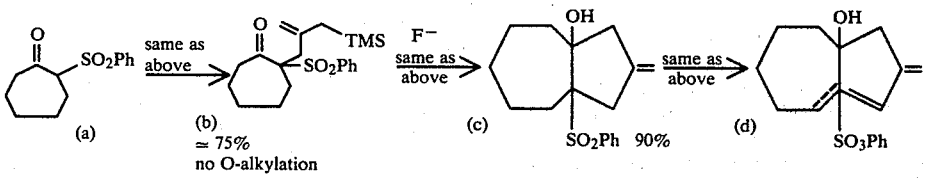

Example 9

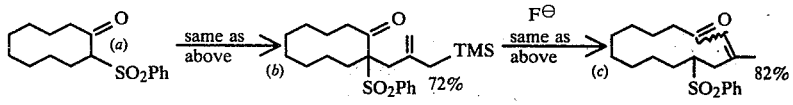

Example 10

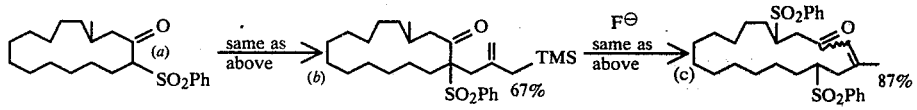

EXAMPLE 11

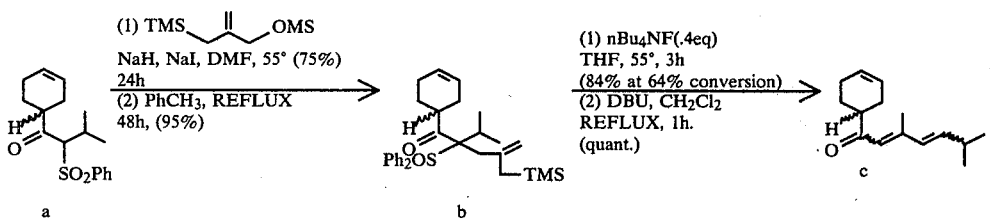

EXAMPLE 5
(a) 3-Benzenesulfonyl-cis-bicyclo[3.3.0]octan-2-one
(b) 2-benzenesulfonyl-3-(2'-trimethylsilylmethyl-2'-propenyl)-cis-bicyclo[3.3.0]octan-2-one
(c) 1-hydroxy-10-methylene-8-benzenesulfonyl-syn,anti,syn-tricyclo[6.3.0.0$^{2,6}$]undecane
(d) 4-methylbicyclo[6.3.0]undeca-3,5-dien-2-one

EXAMPLE 6
(a) 2-benzenesulfonylcyclopentanone
(b) 2-benzenesulfonyl-2-(2'-trimethylsilylmethyl-2'-propenyl)-cyclopentanone
(c) 1-hydroxy-3-methylene-5-benzenesulfonyl-cis-bicyclo-[3.3.0]octane
(d) 3-methylcycloocta-2,4-dienone

EXAMPLE 7
(a) 2-benzenesulfonylcyclohexanone
(b) 2-benzenesulfonyl-2-(2'trimethylsilylmethyl-2'-propenyl)-cyclohexanone
(c) 1-hydroxy-3-methylene-5-benzenesulfonyl-cis-bicyclo-[4.3.0]nonane
(d) 1-hydroxy-3-methylene-bicyclo[4.3.0]non-4 and 5-ene

EXAMPLE 8
(a) 2-benzenesulfonylcycloheptanone
(b) 2-benzenesulfonyl-2-(2'-trimethylsilylmethyl-2'-propenyl)-cycloheptanone
(c) 1-hydroxy-3-methylene-5-benzenesulfonyl-cis-bicyclo[5.3.0]decane
(d) 1-hydroxy-3-methylene-bicyclo[5.3.0]dec-4 and 5-ene

EXAMPLE 9
(a) 2-benzenesulfonylcyclodecanone
(b) 2-benzenesulfonyl-2-(2'-trimethylsilylmethyl-2'-propenyl)-cyclodecanone
(c) 3-methyl-5-benzenesulfonyl-cyclotridec-2-enone

EXAMPLE 10
(a) 2-benzenesulfonyl-14-methyl-cyclopentadecanone
(b) 2-benzenesulfonyl-2-(2'-trimethylsilylmethyl)-14-methyl-cyclopentadecanone
(c) 3,17-dimethyl-5-benzenesulfonyl-cyclooctadec-2-enone

EXAMPLE 11
(a) 1-oxo-1-cyclohex-3'-enyl-2-benzenesulfonyl-3-methyl-butane
(b) 1-cyclohex-3'-enyl-2-benzenesulfonyl-2-isopropyl-4-trimethylsilyl-methyl-pent-4-en-1-one
(c) 1-cyclohex-3'-enyl-3,6-dimethyl-hepta-2,4-dien-1-one It will be apparent that with the mesylate reagent one can achieve chain expansion to add 3 carbons when n is 1, 4 carbons when n is 2, with corresponding expansion of rings when formed thereof. Such chain extension and ring expansion is easily performed by the concepts of this invention when going from $C_5$ to $C_8$ up to from $C_{15}$ to $C_{18}$ except for $C_7$ to $C_{10}$ and $C_6$ to $C_9$, which are difficult to achieve since the change in strain energy is not exothermic. However, the reaction can be made to proceed when change is made in the strain of the ring system.

The expanded ring can be further expanded by the well known Baeyer-Villiger reaction into a macrolide.

It will be understood that changes may be made in the details of formulation and reaction conditions without departing from the spirit of the invention, especially as defined in the following claims.

We claim:

1. The compound having the general formula

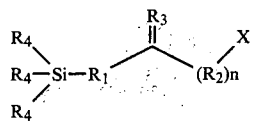

in which n is a number of from 1 to 3, $R_1$, $R_2$, $R_3$ are carbons with or without alkyl substitution, $R_4$ is a $C_1$–$C_{18}$ aliphatic or cyclic group, with or without substituents, and X is a leaving group.

2. The compound as claimed in claim 1 in which $R_4$ is a lower alkyl group.

3. The compound as claimed in claim 1 in which X is a leaving group selected from the group consisting of a halogen and sulfonate ester.

4. The compound 2-X-alkyl-3-allyl trialkyl silane in which X is a leaving group.

5. The compound as claimed in claim 4 in which the leaving group is a halogen or a sulfonate ester group.

6. The compound claimed in claim 4 selected from the group consisting of 2-iodo-methyl-3-allyltrimethyl silane
2-iodo-methyl-3-allyltriethyl silane
2-chloro-methyl-3-allyl-trimethyl silane
2-chloro-ethyl-3-allyl-trimethyl silane
2-sulfonate ester-3-allyl-trimethyl silane
2-iodo-ethyl-3-allyl-trimethyl silane.

7. The method for extension of a ring compound having a keto-sulfone grouping in the ring comprising reacting the keto-sulfone with a reagent compound of claim 1.

8. The method for extension of a ring compound having a keto-sulfone grouping(s) in the ring comprising reacting the keto-sulfone with a reagent compound in accordance with the reaction

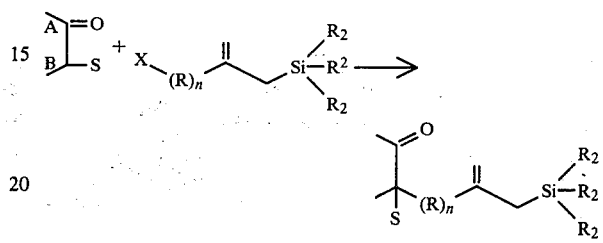

in which A and B are part of a ring structure or not part of a ring structure, X is a leaving group, R is a carbon group, with or without alkyl substitution, n is a number of from 1–3 and $R_2$ is a substituted or unsubstituted $C_1$–$C_{18}$ aliphatic or cyclic group.

9. The method as claimed in claim 7 in which 3 carbons are added when n=1, 4 carbons are added when n=2, and 5 carbons are added when n=3.

10. The method for extension of a ring compound having a keto-sulfone grouping in the ring comprising reacting the keto-sulfone with a 2-X-alkyl-3-allyl-trialkyl silane in solvent solution in the presence of a base such as an alkali metal hydride in which X is a leaving group.

11. The method as claimed in claim 10 in which the reaction is carried out at a temperature within the range of room temperature to 75° C.

* * * * *